United States Patent [19]

Törnblom

[11] Patent Number: 4,646,013

[45] Date of Patent: Feb. 24, 1987

[54] METHOD AND APPARATUS FOR EDDY CURRENT TESTING BY AT LEAST TWO DIFFERENT FREQUENCY SIGNALS

[76] Inventor: Bengt H. Törnblom, Vikhus, Rytterne, S-725 92 Västerås, Sweden

[21] Appl. No.: 680,258

[22] PCT Filed: May 10, 1984

[86] PCT No.: PCT/SE84/00175

§ 371 Date: Nov. 13, 1984

§ 102(e) Date: Nov. 13, 1984

[87] PCT Pub. No.: WO84/04596

PCT Pub. Date: Nov. 22, 1984

[30] Foreign Application Priority Data

May 16, 1983 [SE] Sweden ............................ 8302738

[51] Int. Cl.$^4$ .................... G01N 27/90; G01R 33/12
[52] U.S. Cl. .................................. 324/225; 324/232
[58] Field of Search ............... 324/225, 232, 233, 237, 324/238, 240-242

[56] References Cited

U.S. PATENT DOCUMENTS

| 2,903,642 | 9/1959 | Seigel | 324/330 X |
| 4,061,968 | 12/1977 | Pigeon | |
| 4,303,885 | 12/1981 | Davis et al. | |
| 4,563,644 | 1/1986 | Lenander et al. | 324/232 |

FOREIGN PATENT DOCUMENTS

75078576 7/1975 Sweden .

OTHER PUBLICATIONS

Libby, Hugo L., "Basic Principles," Introduction to Electromagnetic Nondestructive Test Methods, Robt. E. Krieger Pub. Co., Huntington, NY, 1979, Chapter 2, pp. 19–58.

Libby, Hugo L., Introduction to Electromagnetic Nondestructive Test Methods, Robt. E. Krieger Pub. Co., Huntington, NY, 1979, pp. 1–8.

Primary Examiner—Gerard R. Strecker
Attorney, Agent, or Firm—Watson Cole Grindle & Watson

[57] ABSTRACT

During so-called eddy current testing by way of several frequencies, it is often difficult efficiently to separate and detect superficially located defects from the disturbances caused by a varying distance from the transducer to the object under test. This is due to the fact that the fault direction and the lift-off direction normally differ from each other to too small an extent and the fact that the signal processing, which is necessary for the suppression of the lift-off dependence, also suppresses the fault signal. This problem can be eliminated completely or partially by means of the present invention, which comprises selecting the used frequencies in such a way that, in relation to the depths of cracks occurring, they fulfill certain conditions, one of which being that at least one frequency is relatively insensitive to the defect in question. This effect is achieved by selecting such a high frequency that its depth of current penetration is limited seen in relation to the depth of the defect.

5 Claims, 5 Drawing Figures

METHOD AND APPARATUS FOR EDDY CURRENT TESTING BY AT LEAST TWO DIFFERENT FREQUENCY SIGNALS

BACKGROUND OF THE INVENTION

1. Field Of The Invention

A considerable problem in connection with the detection of surface imperfections using, for example, eddy current technique, is the distance dependence (the so-called lift-off dependence) between the transducer and the object under test, which often causes considerable disturbance of the measurements.

2. Prior Art

One method of suppressing the LO dependence is disclosed in Swedish Pat. No. 7507857-6, including the patent of addition.

A similar method is described by Hugo L Libby in "Introduction to Electromagnetic Nondestructive Test Methods". The method of Libby can be regarded as a form of vector transformation technique based on phase discrimination, which means that vectors with different directions are separated with the aid of phase-sensitive/phase-controlled rectifiers.

A *greatly limiting factor* in Libby's method, especially in the practical case involving superficially located defects, for example surface cracks, is that the directions of the fault vectors in the impedance plane (FIG. 3) substantially coincide with the direction/orientation of the LO vectors ($\Delta$LO) (i.e. $\alpha$ is small), thus making it very difficult to efficiently separate the fault vectors (F) from the LO vectors by using phase discrimination only, and simultaneously suppress the lift-off dependence.

For, for example, small/shallow surface cracks the angle ($\alpha$) between the fault direction and the LO direction may only be 10°–15° in case of a hot (1000°) material.

SUMMARY OF THE INVENTION

The present invention aims to provide a solution to the problems mentioned and other problems associated therewith.

The invention can also be regarded as an optimization method, which may then, for example, complement and improve prior art devices, some of which are previously mentioned patented devices. It is thus important to note that the present invention can be regarded both as a device and/or as a method.

DETAILED DESCRIPTION OF A PREFERRED EMBODIMENT

In its function as a device, the present invention can be described as follows. The device, which is primarily intended for testing and/or measurement of electrically conducting test objects (2) with respect to changes (3) in/on the test object, comprises at least one transducer (1), which is supplied with signals, for example current (I), having different frequency contents (e.g. $\omega_H$ and $\omega_L$) so that currents (e.g. eddy currents) of corresponding frequency contents are induced in/on the test objects. The electrical impedance (FIG. 3) of the transducer is then influenced by the test object via the inductive coupling between the transducer and the test object. As a consequence of this, at least two signals, directly or indirectly emanating from the transducer and having different frequency origins (e.g. $\omega_H$ and $\omega_L$), may be signal processed, for example weighted and combined, in such a way that the result, as a function of the distance of the transducer relative to the test object, is constant ($k_1$) within a reasonable operating range, when the test object exhibits no change in or near the transducer, and different from the corresponding result ($k_2$) when there is a change in/on the test object. In this way, the change, for example the surface crack, may be detected and/or be measured as a function of the *difference* and/or quotient between/of the above-mentioned results (e.g. $k_1 - - k_2$ or $k_1 l k_2$).

Characteristic of the type of device referred to is that the equivalent current penetration depth of at least one frequency is smaller than the depth (Dj) of the change or changes being detected.

To describe the problems and how to overcome them, the following example may be used, which should then be understood as one of many feasible examples.

BRIEF DESCRIPTION OF THE DRAWINGS

The above objects, advantages and features of the invention are readily apparent when taken in conjunction with the drawings showing a preferred embodiment of carrying out the invention, wherein:

FIG. 1 shows the transducer/coil (1), assuming two different distances ($LO_2$ and $LO_4$, respectively) relative to the surface of the test object (2). The transducer is supplied with current (I) containing two different frequency components ($\omega_L$ and $\omega_H$). By way of the inductive coupling to the test object, there are thus induced eddy currents of corresponding frequency contents in/on the surface of the test object.

Figure 3:
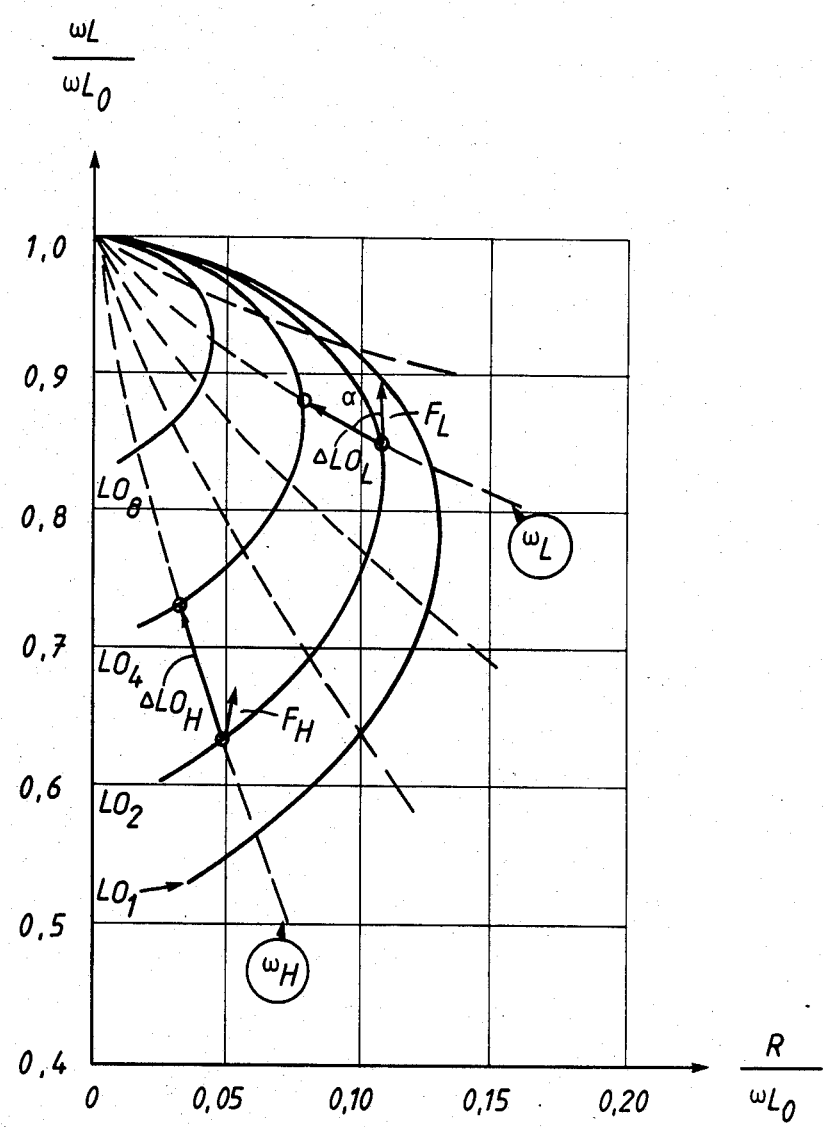
FIG. 3 is a graph of the ratio of $\omega_L/\omega_{LO}$ vs. $R/\omega_{LO}$ showing the fault vectors $F_L$ and $F_H$ for two different frequencies $\omega_L$ and $\omega_H$.

The electrical (standardized) impedance of the transducer will be clear from FIG. 3.

When the transducer changes its distance to the surface of the test object, the impedance of the transducer for the two frequencies with the vectors $\Delta LO_L$ and $\Delta LO_H$ is changed at the same time. If these vectors are made equivalent, for example electronically via different amplification, signals for the two frequencies, which are derived from the transducer, will accompany each other as shown by the functions (G) drawn in soild lines in FIG. 2 ($\Delta U = k_1 = 0$), provided that there is no flaw in the vicinity of the transducer (Dj=0). On the other hand, if a flaw occurs, for example a crack below the transducer (Dj>0), the eddy currents in/on the test object are disturbed to differing degrees at the different-/separate frequencies, whereby $\Delta U \neq 0$, which is an indication of the fact that the test object contains a flaw, for example a crack. This is shown by the dash-lined functions (G) in FIG. 2, where $\Delta U = k_2 > 0$. The vectors $F_L$ and $F_H$ in FIG. 3 represent the fault vector at the frequencies in question ($\omega_L$ and $\omega_H$).

Figure 1:
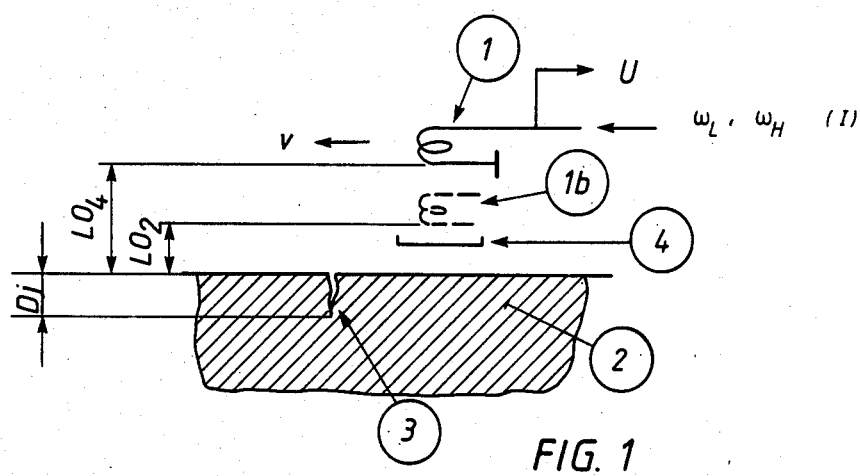
FIG. 1 illustrates a transducer coil at two different distances from a test object for inducing eddy currents therein.
Figure 2:
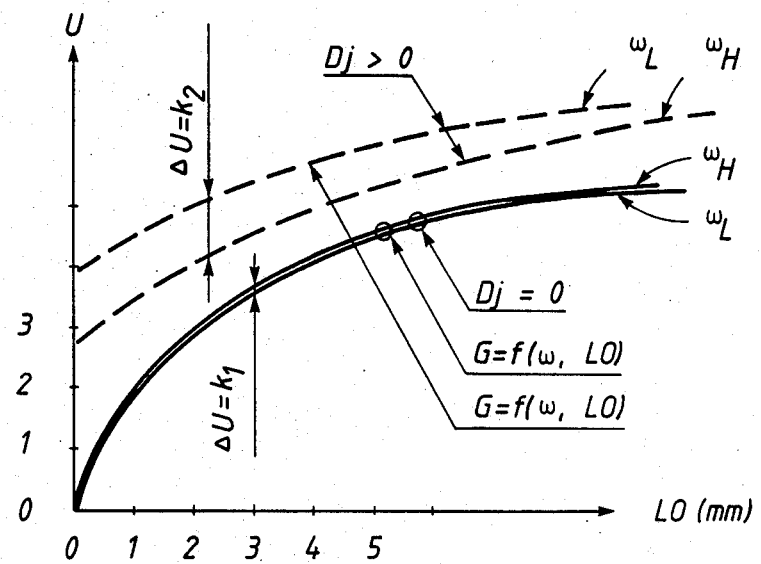
FIG. 2 is a graph of the transducer voltage U vs. the lift-off distance LO.

The results of the signal processing, including possible weighting, etc., are in this case represented by $k_1$ and $k_2$, respectively, in FIG. 2. The difference between the results $k_1$ and $k_2$ indicates the change, for example, the crack. The great problem, however, is that when the signals, which are directly or indirectly received from the transducers, are signal processed (e.g. weighted), *also the other vectors, for example the fault vectors (F), are influenced by the signal processing.* In case of a conventional frequency selection, the consequence of this is that the difference between $k_1$ and $k_2$ is small and difficult to detect, especially in case of small depths of crack (e.g. shallow superficial scratches).

Figure 5:
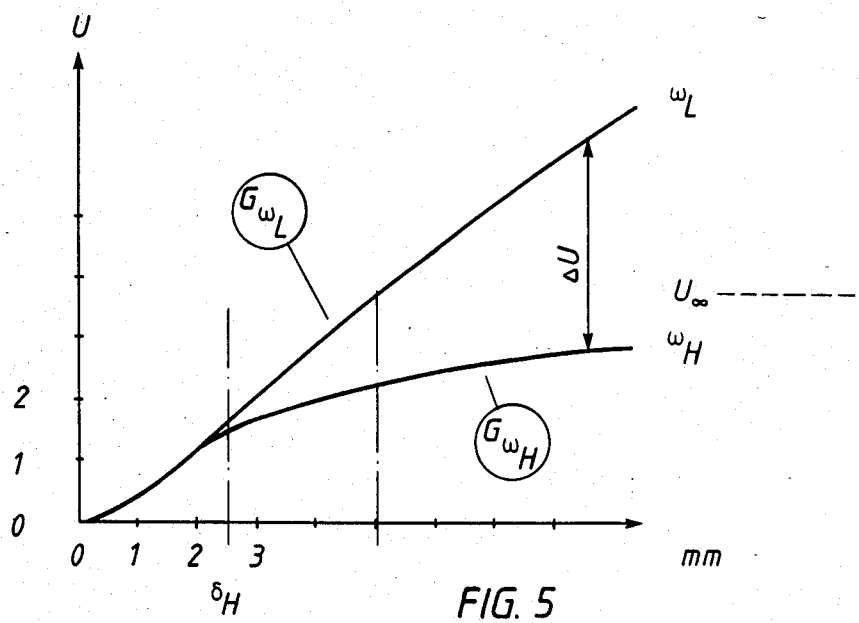

Instead of presenting the G-functions as a function of the lift-off at a constant depth of crack, as in FIG. 2, said G-functions may be shown as a function of the depth of crack at a constant lift-off, as in FIG. 5. In the case where $k_1=0$, the difference $k_2-k_1$ will then be $=k_2$, which then corresponds to $\Delta U$ in FIG. 5. As will be clear from FIG. 5, the difference is very weakly developed at a crack depth (Dj)<2 mm at the frequencies used in this connection. The frequencies are here chosen in a conventional manner, that is to say the crack is to give rise to an optimum fault vector in order—hopefully—to be detected. During difference measurement between the frequencies, however, the result will be negative in case of small crack depths, which is clear from FIG. 5. Another—and perhaps simpler—way of expressing the same thing is as follows. Upon studying FIG. 3 it is seen that the fault vectors are of different magnitudes, that is, $F_L \neq F_H$, but for $k_1$ to become constant when there is no change in the vicinity of the transducer and the distance between the transducer and the test object varies, it is required that $\Delta LO_L$ becomes equally great as $\Delta LO_H$, which requires weighting. This weighting also influences $F_L$ and $F_H$ so that these will be approximately equally great, whereby the difference which is to indicate the defect is suppressed.

Characteristic of the present invention is, among other things, that the difference between the results (e.g. $k_1$ and $k_2$) should be prevented from becoming too small by using frequency selection optimization. To attain this effect, priority has been given to the following partial objectives:

(a) for at least one frequency or complex of frequencies, a *great* lift-off dependence and a *small* fault dependence are aimed at in so far as the vector amounts in question are concerned, and (b) seen in relation to item (a), for at least one frequency or complex of frequencies, a *small* lift-off dependence and a *great* fault dependence are aimed at.

From FIG. 3 it will be clear that the objective according to the above item (a) largely corresponds to $\omega_H$ and that item (b) corresponds to $\omega_L$.

The greater the difference in the relationship between these frequencies, the better will also the difference stand out (e.g. $k_1-k_2$), provided that the frequencies are suitably located along the frequency axis.

Figure 4:
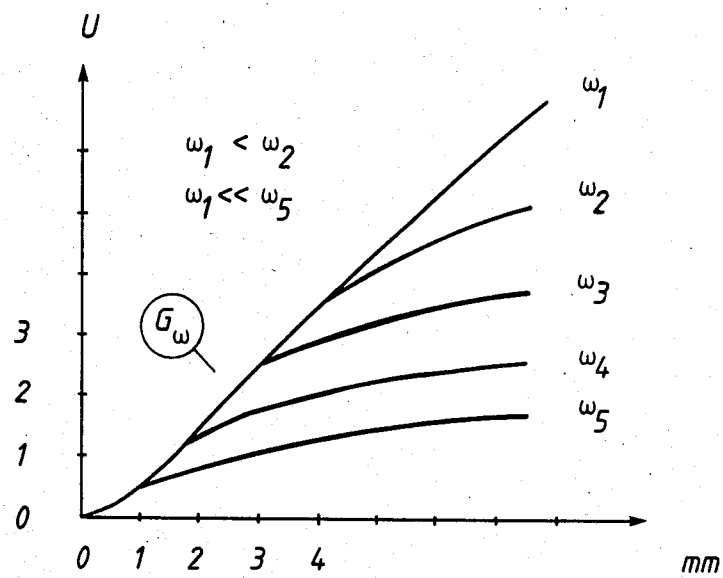
FIGS. 4 and 5 respectively show various plots of transducer voltage U vs. depth of penetration of the inducted eddy currents for various frequencies and for $\omega_H$ and $\omega_L$.

FIG. 4 shows how the difference may differ between a few different frequencies. In other words, FIG. 4 shows the same as FIG. 5, but with different frequencies.

In FIG. 5, $G\omega_L$ and $G\omega_H$ are functions of output signals from, for example, parallel carrier frequency channels ($\omega_L$ and $\omega_H$, respectively), which in practice often have different amplification.

This means that the functions $G\omega_L$ and $G\omega_H$ may have different inclination, for example in accordance with FIG. 5.

The relationship $G\omega_L/G\omega_H$ is, however, constant and is called $k_K$ (the difference $\Delta U$ is not constant).

$$k_K = \frac{G\omega_L}{G\omega_H}$$

With the aid of the new constant $k_V$, we arrive at the following: $G\omega_L=G\omega_H$. If we introduce a new amplification constant $k_V$, which is 0.5, we obtain $0.5 \cdot 2G\omega_H = G\omega_H$, and thus $G\omega_L = G\omega_H$, which gives two coinciding functions (see FIG. 2). FIG. 2 shows the same functions as FIG. 5 but weighted with $k_V$. In this case, $\Delta U$, i.e. the difference, is constant. It is important to note that the functions $G\omega_H$ and $G\omega_L$ do not necessarily include any form of phase discrimination; however, this may, of course, be included if it is appropriate in some special case.

In FIG. 5, the curves $\omega_L$ and $\omega_H$ represent the direct or indirect transducer signals (G) originating from the frequencies $\omega_L$ and $\omega_H$ (after weighting and signal processing for obtaining suppression of the position). The relation between the frequencies is here chosen greater than 10 ($\omega_H/\omega_L > 10$), and the equivalent depth of current penetration ($\delta_H$) for $\omega_H$ is marked. What is of great interest here is why the difference $\Delta U$ starts to develop at the crack depths (Dj) which approximately correspond the depth of current penetration $\delta_H$. The explanation of this is very complicated, and therefore the following popular and simplified explanation will have to serve as guidance. When the crack depth (Dj) is greater than the current penetration, that part of the crack which is positioned deepest (the bottom portion) only influences the eddy current paths to a relatively small extent, while at the same time these deep-travelling currents are small (possibly non-existent). The inductive coupling between these deep-going currents and the transducer coil is also small, among other things because of the larger distance to the transducer coil. All these facts taken together cause the influence of the crack on the transducer impedance to be reduced, relatively seen, which is the explanation of the difference starting to develop at/around the equivalent depth of current penetration for the high frequency.

The consequence of the above reasoning is then that the objective according to item (a) is fulfilled if $\omega_H$ is chosen so that its equivalent depth of current penetration is smaller than the defect, for example surface crack, which is to be detected, that is, $\delta_H < Dj$ or, even better, $\delta_H <<< Dj$.

Since the above reasoning is one of the corner stones of the invention, additional clarifications and examples may be justified to increase an understanding. On viewing FIG. 5 (which is verified in practice) and increasing the fault depth from zero, the G$\omega$-functions first accompany each other as long as the crack depth is smaller than $\delta_H$, and are then separated. The reason for this is that as long as the crack is small, it forces down the superficial currents to an approximately equivalent extent for both frequencies. Somewhat simplified, the transducer interprets this as a lift-off variation. (From this follows that $\alpha$ will be small.) One condition for this is, of course, that the functions are weighted with respect to the suppression of the distance dependence!

This mutual agreement between the frequencies as far as the connection between lift-off dependence and fault dependence is concerned is difficult to present in the form of mathematical derivations, but even simple reasonings combined with practical measurements support in full the statement that these relatively refined physical relationships apply. In other words, the deviations are surprisingly small in the practical case.

Turning back to the fault/crack, the eddy currents around the crack are disturbed, resulting in the current displacement being disturbed as well. This results in the current penetration becoming somewhat deeper near the crack. The consequence of this is that $G\omega_H$ does not deflect sharply but relatively softly. Now, if the crack depth is increased successively so that $Dj >> \delta_H$, $G\omega_H$ should asymptotically approach a U-value ($U\infty$) corresponding to $Dj = \infty$. The same should be true of $G\omega_L$ but at a greater depth of fault.

This can also be expressed such that in case of large fault depths relative to $\delta_H$, the influence on the transducer impedance is small at $\omega_H$ for the deeper part of the fault. In practice this can be utilized to separate the *amount* of the fault vectors, whereby the need of a perfect phase discrimination for separation of the LO vector and the fault vector from each other is eliminated. Looking at FIG. 3, it is seen that $\Delta LO$ increases with increasing frequency. To obtain suppression of the distance dependence, the amplification for $\omega_H$ can then, for example, be reduced ("weighting") so that $\Delta LO_L = -\Delta LO_H$. This then strenghtens the difference ($\Delta U$) in FIG. 5, where this has been taken into consideration! It is therefore important once again to stress that FIGS. 4 and 5 show a new, unique method of obtaining, via frequency difference measurement starting from the position suppression, a detectable difference representing the fault.

As will be clear from the description, the device/-principle is primarily designed for superficially located cracks, and the like. The cracks which are located deep down and do not extend to the surface can often be detected by conventional methods since these exhibit a greater difference in phase relative to the lift-off vectors.

From FIG. 5 it is further clear that only at a crack depth <5 mm has there been developed a marked and clear difference, that is, at $2 \times \delta_H$ the difference is clear. From this follows that $\omega_H$ should be chosen so that $\delta_H << Dj/2$ and $\delta_L < Dj$. Since $\delta \sim 1/\sqrt{\omega}$, the relation $\omega_H/\omega_L$ should be chosen so that $\omega_H/\omega_L > 2^2$, that is, $\omega_H/\omega_L > 4$.

It should be noted that, as in the previous case, the reasoning refers to the position suppression, which is the basis/starting point of the invention.

The assumptions $\delta_H < Dj/2$ and $\delta_L > Dj$ also show that the frequency selection should be made so that the absolute value of the frequencies refers to $\delta$ and, thus, also to the crack depth of the smallest cracks to be detected. Both the relationship between the frequencies and the absolute values are, thus, of the greatest importance for the result of the measurement.

Neither Libby nor Swedish Pat. No. 7507857-6 indicates or describes technique that can be employed to overcome the problems stated in this patent application, in spite of the fact that both these methods/devices suffer from the limitations described here.

It is important to point out that the present invention can be combined with other methods and/or devices. Therefore, for example, the method of Libby can be combined with the frequency selection optimization described here, or the frequencies stated in Swedish Pat. No. 7507857-6 may be selected according to the method described in the present invention, whereby the difference (e.g. $k_2$) can be further amplified. This underlines the nature of a complementary special case. In addition to phase discrimination, also weighting, linearization, standardization, vector transformation, and so on, as described in the above-mentioned patent publications, may be regarded as branches of technique which may be combined with the present invention.

To obtain the desired damping of, for example, $G\omega_H$ in FIG. 5, and thus a well developed difference $\Delta U$, higher frequencies that what is normal in conventional methods are required. This consequence is especially noticeable when detecting defects on hot (e.g. >750° C.) steel because of the low electrical conductivity of the steel at these temperatures. In order for the current penetration depth ($\delta$) to be smaller than the crack depth (Dj), frequencies >>1 MHZ are often required for small crack depths. To be able to handle these relatively high frequencies in practice, it is often advantageous to locate certain electronic adaptation equipment, etc., in proximity to the transducer (1). Similarly, any shielding material (4) adjacent the transducer, for example cooling diaphragms, and the like, should be of ceramic material, or the like, in order not to attenuate or otherwise influence the high frequencies to too great an extent.

The scope of the present invention also includes the following modifications. The signals emanating from the transducer may, for example, also be obtained via/-from circuits of which the transducer forms a part. Examples of this are oscillators, the frequency and amplitude of which are then determined by, among other things, the impedance of the transducer. Thus, in principle, the difference between current results (e.g. $k_2 - k_1$) can be obtained as the difference between two frequencies or between two signal-processed frequencies. However, it should be realized that, directly or indirectly, it is always the impedance of the transducer that forms the basis for these special modifications.

The transducer may, for example, also consist of several coils, which, for example, are individually supplied with a different frequency.

Signal processing and other electronics functions may, of course, be accomplished by using computers and the like. The signal processing may also be supplemented with a utilization of, for example, position signals obtained in a different way (from what is stated here), for example from a separate position transducer.

To sum up, the fact that the fault direction and the LO-direction often differ very insignificantly ($\alpha$) from each other, and that the signal processing which is required for the suppression of the LO-dependence usually also suppresses the difference/deviation which is to indicate the change, renders it difficult to detect, by means of conventional so-called multi-frequency methods/devices, changes such as surface cracks, etc., while maintaining the suppression of the LO-dependence. This problem can be eliminated with the present invention, which comprises optimizing the frequencies used, that is, selecting such frequencies in relation to the crack depth in question that they fulfil certain conditions, one of which being that at least one frequency is relatively *insensitive* to the defect in question. This effect is achieved by selecting such a high frequency that its current penetration depth is limited seen in relation to the depth of the defect, for example a crack.

The figures accompanying the description are only examples showing the principle, which means that they are not always, for example, drawn according to scale.

In normal cases the frequency is increased to make it possible to *better* detect the fault (because of a more distinct current displacement). In the present invention, the frequency is increased further to obtain a *deteriorated* sensitivity to the fault (and, if possible, a better sensitivity to lift-off), which indicates a fundamentally important difference between the prior art and the present invention.

The invention can be varied in many ways within the scope of the appended claims.

Some of the more important definitions will be clear from the following summary:

By TRANSDUCER is meant, for example a magnetic flux-generating unit and a magnetic flux-sensing unit comprising at least one coil or wire loop. In principle, a coil supplied with current may be both flux generating via the number of ampere turns and flux sensing via the coil impedance. The transducer may also advantageously consist of a primary coil supplied with current and a sensing secondary coil in which an e.m.f. is induced. This e.m.f. will then also contain information about disturbances in the propagation of eddy current, etc.

By TEST OBJECT are meant, for example, plates, billets, tubes, wire, rod, etc.

By CHANGE are meant, for example, defects, cracks, holes, flakes, etc.

By DIFFERENCE is meant, for example, the difference between $k_1$ and $k_2$ in FIG. 2. However, DIFFERENCE also relates to the quotient, that is, the relationship between $k_1$ and $k_2$.

By CONSTANT is meant largely constant within a reasonable operating range.

By FREQUENCY is usually meant the frequency or frequency component with which the transducer is supplied. The term frequency also comprises a complex of frequencies.

By LIFT-OFF (LO) is meant the distance between the transducer and the test object.

By WEIGHTING and LINEARIZATION are meant, for example, the following. In FIG. 2 the curves shown in unbroken lines represent functions which are derived from the frequencies $\omega_L$ and $\omega_H$. If these functions are designated $G\omega_L$ and $G\omega_H$, the relationship between them is often substantially constant within a reasonable operating range due to physical factors and similarities between the frequencies, that is, $G\omega_L/G\omega_H=k_k$, where $k_k$ represents a quotient constant.

By introducing a new weighting constant $k_v$, the magnitude of which is determined by the fact that $k_k \times k_v = 1$, the above-mentioned quotient can be transformed into a constant difference by weighting with the constant $k_v$. Or, expressed in simpler terms, $k_v \times G\omega_L = k_v \times k_k \times G\omega_H = 1 \times G\omega_H$, that is, if $k_v$ is incorporated into G, the G-functions will coincide with each other after weighting with $k_v$. This shows that a constant quotient constant ($k_k$) can always be weighted with a real or imaginary weighting constant ($k_v$) so that the constant quotient may be regarded as a constant difference.

In those cases where the difference $k_1$ in FIG. 2 is not constant at certain points, some of or both of the G-functions may be linearized so that the difference $k_1$ is constant over the entire operating range (by means of e.g. function generation).

By CURRENT PENETRATION DEPTH is meant the equivalent current penetration depth, that is, the depth where the field strength/current intensity has dropped to $1/e = 36.8\%$ relative to the surface.

By $\omega_H$ and $\omega_L$, respectively, are meant high and low frequencies, respectively.

By "in close proximity to the transducer" is meant that the electronic equipment is installed, for example, a few meters from the transducer separate from the other electronic equipment.

I claim:

1. A method for testing electrically conducting test objects for defects therein, comprising:

exciting a transducer with signals of different frequencies to induce eddy currents in said test object;

deriving at least two test signals from said transducer such that the quotient of said at least two test signals is substantially constant as a function of the distance of said transducer from the surface of said test object;

selecting one transducer frequency excitation to produce a current penetration depth less than a specified penetration depth;

selecting the lowest transducer excitation frequency to provide a current penetration depth at least three times greater than the depth of a second specified detection depth; and detecting a defect by forming a quotient between said at least two test signals, thereby determining such defects with small angle relationships between the fault vector and the lift-off vector.

2. Apparatus for testing electrically conducting test objects for defects therein, comprising:

at least one transducer excited by signals of different frequency to induce eddy currents in said test object;

means for detecting said eddy currents to produce at least two signals having at least partially different frequency content, the quotient of said at least two signals having a substantially constant relationship with respect to one another as a function of the distance of said at least one transducer from the surface of said test object with no detection of a defect therein, and the quotient of said at least two signals having a substantially different relationship in the presence of a defect;

at least one of said signals of different frequency produces an eddy current penetration depth smaller than the depth of specified defects;

the lowest signal frequency producing an eddy current penetration depth at least three times greater than another specified depth; and means for determining a defect by a predetermined difference in the quotient of said at least two signals, thereby determining such defects with small angle relationships between the fault vector and the lift-off vector.

3. Apparatus as claimed in claim 2 wherein said test object has a temperature greater than 700 degrees centigrade and that at least one frequency is greater than 100 KHz.

4. Apparatus as claimed in claim 2 wherein said means for detecting are positioned in close proximity to said at least one transducer.

5. Apparatus as claimed in claim 2 further comprising an insulator containing aluminum oxide is positioned between said at least one transducer and said test object.

* * * * *